United States Patent [19]
Gravener et al.

[11] Patent Number: 5,160,678
[45] Date of Patent: * Nov. 3, 1992

[54] PRESSURIZED POWDER SUPPORT FOR TREATING PROCESSES

[75] Inventors: Roy D. Gravener, Southport; Ross R. Muth, Brookfield, both of Conn.

[73] Assignee: United States Surgical Corporation, Norwalk, Conn.

[*] Notice: The portion of the term of this patent subsequent to Nov. 3, 2009 has been disclaimed.

[21] Appl. No.: 643,911

[22] Filed: Jan. 18, 1991

Related U.S. Application Data

[63] Continuation of Ser. No. 451,416, Dec. 15, 1989, abandoned.

[51] Int. Cl.[5] .................... B29C 35/00; B29C 43/12
[52] U.S. Cl. .................. 264/101; 264/313; 264/320; 264/346; 264/235; 264/DIG. 50; 264/571; 425/405.2
[58] Field of Search ............. 264/235, 346, 101, 102, 264/570, 571, 572, 320, DIG. 50, 313, 314, 325; 425/388, DIG. 10, 405.1, 405.2

[56] References Cited

U.S. PATENT DOCUMENTS

| | | | |
|---|---|---|---|
| 1,582,233 | 4/1926 | Aiken . | |
| 2,021,666 | 11/1935 | McQuaid . | |
| 2,395,675 | 2/1946 | Luth . | |
| 2,488,922 | 11/1949 | Mead | 264/342 |
| 2,499,324 | 2/1950 | Mead | 264/339 |
| 2,909,417 | 10/1959 | Osenberg | 51/298 |
| 3,135,640 | 6/1964 | Kepka et al. | 156/147 |
| 3,249,964 | 5/1966 | Shaler | 425/405.2 |
| 3,363,037 | 1/1968 | Levey, Jr. et al. | 425/405.2 |
| 3,830,607 | 8/1974 | Baxendale et al. | 425/405.2 |
| 4,060,704 | 1/1978 | Wittmoser | 425/405.2 |
| 4,264,556 | 4/1981 | Kumar et al. | 264/314 |
| 4,415,523 | 11/1983 | Barham et al. | 264/342 |
| 4,416,266 | 11/1983 | Baucom . | |
| 4,422,999 | 12/1983 | Mitchell | 264/339 |
| 4,591,630 | 5/1986 | Gertzman et al. | 528/503 |
| 4,640,711 | 2/1987 | Lichti et al. | 264/DIG. 50 |
| 4,755,343 | 7/1988 | Kromrey | 264/DIG. 50 |
| 4,770,835 | 9/1988 | Kromrey | 264/546 |

FOREIGN PATENT DOCUMENTS

| | | |
|---|---|---|
| 72232 | 2/1983 | European Pat. Off. . |
| 202090 | 11/1986 | European Pat. Off. . |
| 278180 | 8/1988 | European Pat. Off. . |
| 3418110 | 11/1985 | Fed. Rep. of Germany . |
| 57-146607 | 9/1982 | Japan . |
| 89/01376 | 2/1989 | PCT Int'l Appl. . |
| 1264139 | 2/1972 | United Kingdom . |

*Primary Examiner*—Jan H. Silbaugh
*Assistant Examiner*—Mathieu Vargot
*Attorney, Agent, or Firm*—Thomas R. Bremer; Peter G. Dilworth; Rocco S. Barrese

[57] ABSTRACT

A method for supporting a piece which is to undergo a treatment process including embedding the piece in a particulate support medium, enclosing the support medium in a container, and pressurizing the support medium by applying pressure to the outside of the container or by applying a vacuum to the interior of the container. Various treatment processes may be employed, such as annealing.

26 Claims, 5 Drawing Sheets

PRESSURIZED POWDER SUPPORT FOR TREATING PROCESSES

This is a continuation of Ser. No. 07/451,416, filed on Dec. 15, 1989, now abandoned.

BACKGROUND OF THE INVENTION

1. Field Of The Invention

This invention relates to supporting a fabricated piece for purposes of treating said fabricated piece and in particular to a method for supporting a thermoplastic piece for annealing.

2. Background Of The Art

Methods for annealing plastics are commonly known in the art. In general, plastics are annealed to remove residual stresses and strains, to stabilize the shape of a plastic piece, and to reduce or eliminate defects in the piece. After forming a plastic piece by means of injection molding or extrusion, residual flow induced stresses may remain in the piece, as well as stresses from the differential density, shrinkage, and the viscoelastic behavior of the plastic during nonuniform cooling. Stresses are usually induced by quickly cooling a polymer from above its glass transition temperature. Molded thermoplastics containing residual stresses are more likely to develop stress crazing and stress cracking. To alleviate the effects of internal stresses, plastic pieces are usually annealed. Annealing typically comprises reheating the plastic to above its glass transition temperature where chain mobility is greatest, and then slowly and gradually cooling the plastic to avoid reintroducing stresses. Plastic which is heated above its glass transition temperature usually relieves internal stresses by changes in density and specific volume.

Moreover, some degree of crystallization of the plastic may be achieved by heating it to a temperature above its glass transition temperature. Consequently, a freely held piece will often undergo distortion and shrinkage. Presently used equipment for annealing plastic usually comprises either liquid baths or hot air. Liquid bath methods using water, oil or waxes, usually make some provision for recycling the liquid to prevent temperature build-up or hot spots. Air flow methods usually employ circulating-air or air flow ovens. Other methods such as using convection ovens infrared ovens, and dielectric (e.g. microwave) ovens are also employed. Generally such methods require means such as racks or clamps to hold or suspend the plastic piece in the annealing oven.

Plastic pieces used in surgical procedures often have complicated structures and must operate in conditions where close tolerances are required. Even small distortion or shrinkage in plastic pieces such as surgical fasteners is undesirable. Racks or simple clamping means are not effective for eliminating distortion or shrinkage, hence the use of fixturing, which involves supporting the plastic piece along substantially its entire external surface, usually by placing the plastic piece in a device closely resembling the mold from which the piece was originally fabricated. Pieces which have fine surface detail require expensive fixtures to match and support the detailed configuration of the piece.

Annealing is but one example of various processes which require a work piece to be supported in this manner. Other treating processes which require access to the surface of the work piece, such as those entailing chemical reactions, diffusion, coating, etc., often cannot be efficiently performed with the customary fixturing apparatus and methods.

To overcome problems such as those described above, the present invention provides a novel and inexpensive method to support a work piece for undergoing treatment processes, such method providing support over substantially the entire surface of the work piece while allowing access to the surface for various treatment and conditioning processes. The invention further provides a unique method for supporting a work piece having at least one hollow or cut-out section either internally or externally so as to maintain an equilibrium between internal and external pressure forces applied to the work piece. The invention also provides a surgical fastener constructed of a material treated in accordance with the method disclosed herein.

SUMMARY OF THE INVENTION

A method is provided herein for supporting an object to be treated comprising placing the object within a particulate support medium, and compacting the support medium into a rigid mass by applying pressurizing means to create a difference between the pressure outside the particulate support medium and the pressure inside the particulate support medium. The pressurizing means can comprise reducing the pressure inside the support medium as, for example, by applying a vacuum to the interior of the support medium, preferably with an inside pressure of less than 1 torr. The support medium is optimally contained within a flexible container such as a flexible bag if application of a vacuum is the pressurizing means. The pressurizing means also can comprise increasing the pressure outside the particulate support medium such as by applying pressure to the particulate support medium by a piston means wherein the piston means is hydraulically driven, pneumatically driven, spring driven, or driven by deadweight. The particulate support medium is ideally contained in a rigid container if a piston means is employed. The object can then be treated by, for example, annealing the object. The particulate support medium can comprise powdered talc, or sodium bicarbonate, preferably sodium bicarbonate which has been conditioned by treating for about 12 hours at about 125° C., or any other suitable particulate material.

An alternative embodiment provides a method for supporting an object for a treating process comprising placing the object within a particulate support material, enclosing the object and particulate support material within a rigid container which is sealed on all sides, the particulate support material and the container having different coefficients of thermal expansion, and compacting the particulate support medium by changing the temperature of the support medium and the container. Wherein the particulate support material has a coefficient of thermal expansion greater than that of the container, changing the temperature is accomplished by heating the container and particulate support medium. Wherein the particulate support medium has a coefficient of thermal expansion less than that of the container, changing the temperature comprises cooling the container and particulate support medium.

BRIEF DESCRIPTION OF THE DRAWINGS

Preferred embodiments of the present invention are described hereinbelow, wherein.

DETAILED DESCRIPTION OF THE INVENTION

The method of the present invention utilizes a pressurizing means to compress a body of particulate support medium in which a piece to be treated is embedded.

The work piece contemplated is any object on which it is desired to effect a treatment process. A preferred work piece is constructed of an annealable material such as molded thermoplastics, or the like. In particular, the application of the method of the present invention to bioabsorbable surgical fastener is contemplated.

Although the pressurized powder support of the present invention is particularly suitable for annealing, other methods of treatment which entail coating a work piece, diffusion of materials into or out of the work piece, chemical reactions with the work piece, etc. are also contemplated as being within the scope of the present invention.

"Pressurizing" is defined as establishing a pressure difference such that the pressure external to the body of particulate medium is greater than the pressure internal to the body of particulate medium, thereby resulting in compression of the medium. Such pressurizing may be achieved by increasing the external pressure or by decreasing the internal pressure.

Increasing the external pressure may be accomplished, for example, by a piston actuated by hydraulic or pneumatic means, by spring mechanism, or by a dead weight applied to the piston. Another way to increase the external pressure is by a pre-stressed membrane, i.e. for example placing the particulate medium in a pre-stretched elastic membrane and then allowing the membrane to contract.

Decreasing the internal pressure may be accomplished by applying a vacuum to the interior of the particulate medium. A preferred method for the use of an evacuated powder support medium for treatment processes is described below.

Figure 1:
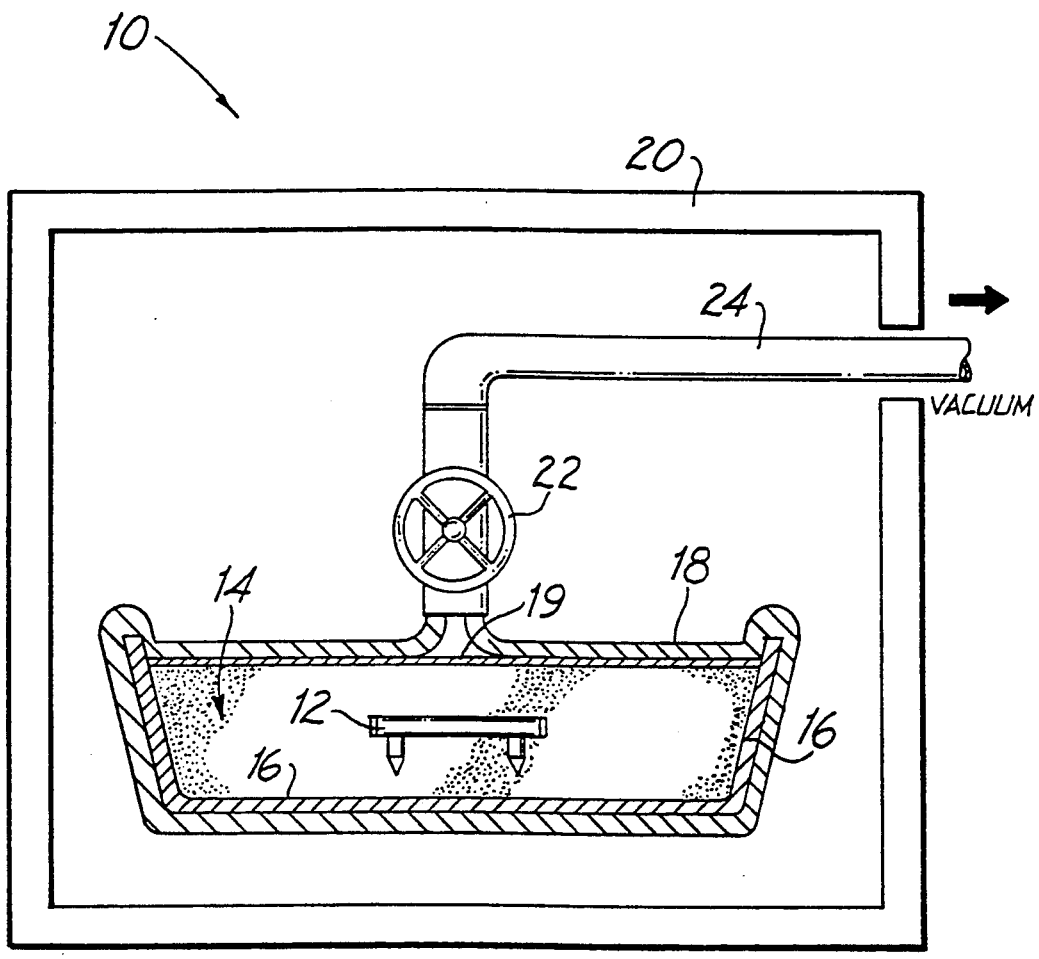
FIG. 1 is a diagrammatic elevational view partially in cross section of an apparatus employing the vacuum method of the present invention.

Referring to FIG. 1 the thermoplastic work piece 12 to be annealed is embedded in a finely divided support medium 14 contained within a pan or receptacle 16. Work piece 12 may be of any shape or configuration and is generally produced from an injection molding process. The support medium 14 may be any inert powder of suitable particle size to rigidly support the piece. Because work piece 12 may be only a few millimeters in size, and of relatively complex shape, it is important that the particle size of powder 14 be sufficiently small relative to the work piece so as to enable the powder to conform to and to support the intricate surface detail of piece 12. Powdered talc has been found to be useful. However, it is preferable to employ a powder which is water soluble and can be washed free from the piece 12 after annealing. For example, sodium bicarbonate has been found to be an effective support medium. The sodium bicarbonate powder is preferably conditioned by heating in an oven in flat pans at about 125° C. for about 12 hours, whereby it is largely converted to the carbonate. The powder is then cooled and sifted through #20 standard mesh screen and stored dry.

The particles of the support medium 14 are able to flow around work piece 12 and to conform to the details of the exterior surface of the piece. A fine mesh screen 19 is positioned above the layer of support medium 14 to prevent it from being drawn out by the vacuum. The pan 16 containing the support medium 14 and embedded piece 12 is placed into a flexible air tight vacuum bag 18. Vacuum bag 18 may completely envelop pan 16 although this is not essential, provided that a substantially airtight enclosure of support medium 14 is accomplished. The apparatus is placed in oven 20 and connected to a vacuum line 24 by means of valve 22, and a vacuum is applied to the interior of bag 18 to reduce the interior pressure preferably to about 1 torr.

The application of a vacuum to bag 18 serves to create a pressure differential between the interior and exterior of bag 18. Thus, for example, if the external pressure is a standard atmosphere, i.e. 760 torr, reducing the pressure within bag 18 through the application of a vacuum to 1 torr will create a pressure differential of almost one atmosphere. The maximum pressure differential obtainable by vacuum means alone is atmospheric pressure, or about one atmosphere. However, higher pressure differentials may be achieved by increasing the external atmospheric pressure, e.g. by placing bag 18 in a pressure oven. Thus, alternative methods (i.e. increasing the pressure of the surrounding atmosphere, and decreasing the internal pressure) may be used singly or in conjunction with each other to achieve a broad range of pressure differences. The ability to adjust the pressure differential is a highly desirable feature since the work pieces to be treated or the treatment processes to be employed may have characteristics which require certain pressure differences or certain internal pressures.

Preferably, a vacuum bag sealer (not shown) may be used to maintain the vacuum within bag 18. After drawing the vacuum, bag 18 is sealed as a unit. Disposable plastic bags may be employed. Use of a vacuum bag sealer eliminates the need for the bag to be constantly attached to a vacuum source. When the interstitial air is evacuated the particles of the support medium 14 are compacted into a rigid mass for as long as the vacuum is maintained. Thus, the powder 14 which was once fluid is temporarily rigidified into an inflexible mold-like support which presents an inner surface conforming in exact detail to the shape of work piece 12.

Figure 2A:
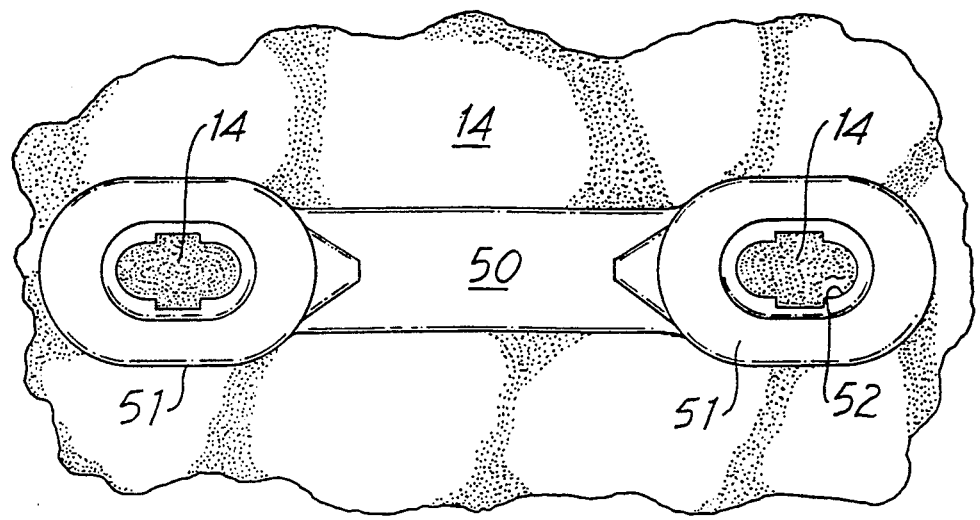
FIG. 2a and 2b are plan and elevational views, respectively, of a retainer portion of a two part surgical fastener in a powder support.
Figure 2B:
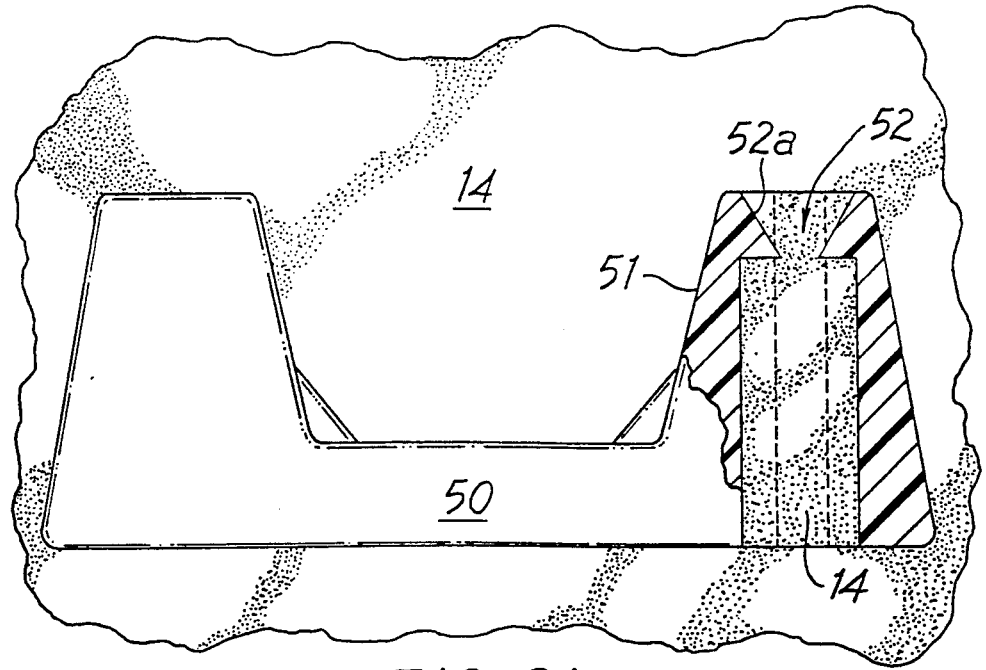
Figure 4A:
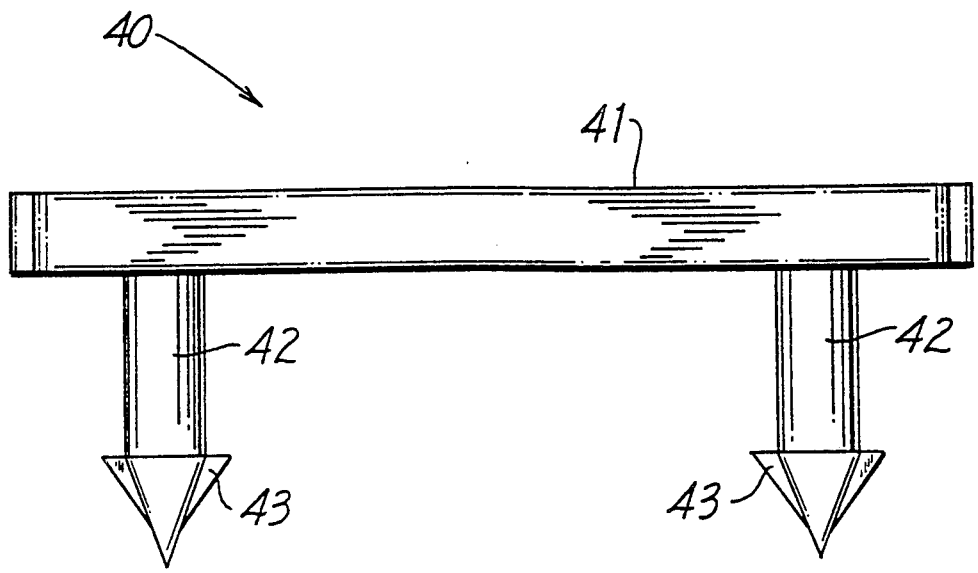
FIGS. 4a and 4b are elevational and bottom views, respectively, of a surgical fastener annealed in accordance with the method of the present invention.
Figure 4B:
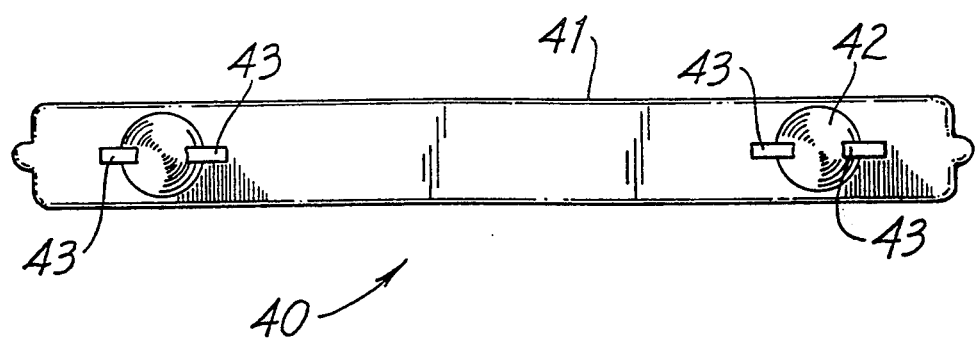

A preferred application of the method of the present invention is directed to annealing surgical fasteners such as fastener 40 illustrated in FIGS. 4a and 4b, and retainer portion 50 of a two part surgical fastener as illustrated in FIGS. 2a and 2b. Such fasteners are often molded from thermoplastic materials which are bioabsorbable (i.e. absorbed by the human or animal body in which they are implanted). Because of the particularly sensitive environment and use contemplated by such fasteners, it is of utmost importance to anneal them to eliminate potential defects and stresses which would present unnecessary danger to patients. As noted hereinabove, however, although such surgical fasteners are contemplated as a preferred application of the instant method, it is clearly applicable to all products constructed of thermoplastic materials where annealing is necessary or desirable.

One of the advantages of the method of the present invention is that the powder support medium can fill the hollow spaces of the interior of a piece so that when the powder support medium is pressurized, the powder medium in the interior to the work piece is pressurized as much as the powder exterior to the work piece, thereby establishing a pressure equilibrium. FIG. 2a illustrates in plan view a retainer portion 50 of a two part surgical fastener, which is embedded in the powder support medium 14. FIG. 2b illustrates the retainer 50 in elevational partially sectional view. As can be seen the powder medium 14 enters and fills the hollow channel 52 extending through columnar members 51. Because the powder medium is often poured or sprinkled from above the container 16, it is often advantageous to facilitate entry of the powder 14 into a hollow space by orienting the work piece such that the powder naturally falls into the hollow channel. Thus, retainer 50 is preferably oriented so that the opening 52a of hollow interior channel 52 is aligned with the inflow of powder medium 14, i.e. by being placed vertically upright. Powder 14 fills the channel 52 as it is being poured into container 16 and exerts pressure on the interior walls of the column to balance external pressure.

Referring again to FIG. 1, if it is desired to anneal a work piece 12, oven 20 may be heated and held at a temperature and time sufficient to anneal the polymer. The appropriate temperature and heating time will depend upon the type of thermoplastic resin from which the plastic piece is constructed, the size and shape of the piece, the heating characteristics of the apparatus and support medium, etc. Convection heating is generally used, but other types of heating such as dielectric heating, microwave heating, etc. may also be employed.

When the heating has been completed, the apparatus is allowed to cool slowly to ambient or room temperature. The contents of the pan 16 are removed and separated by, for example, sifting on a standard mesh screen to separate the plastic work piece 12 from the powder 14. If a water soluble powder is used, such as sodium bicarbonate, piece 12 can be quickly rinsed in water to remove any traces of powder, then vacuum dried to remove the water.

Figure 3:
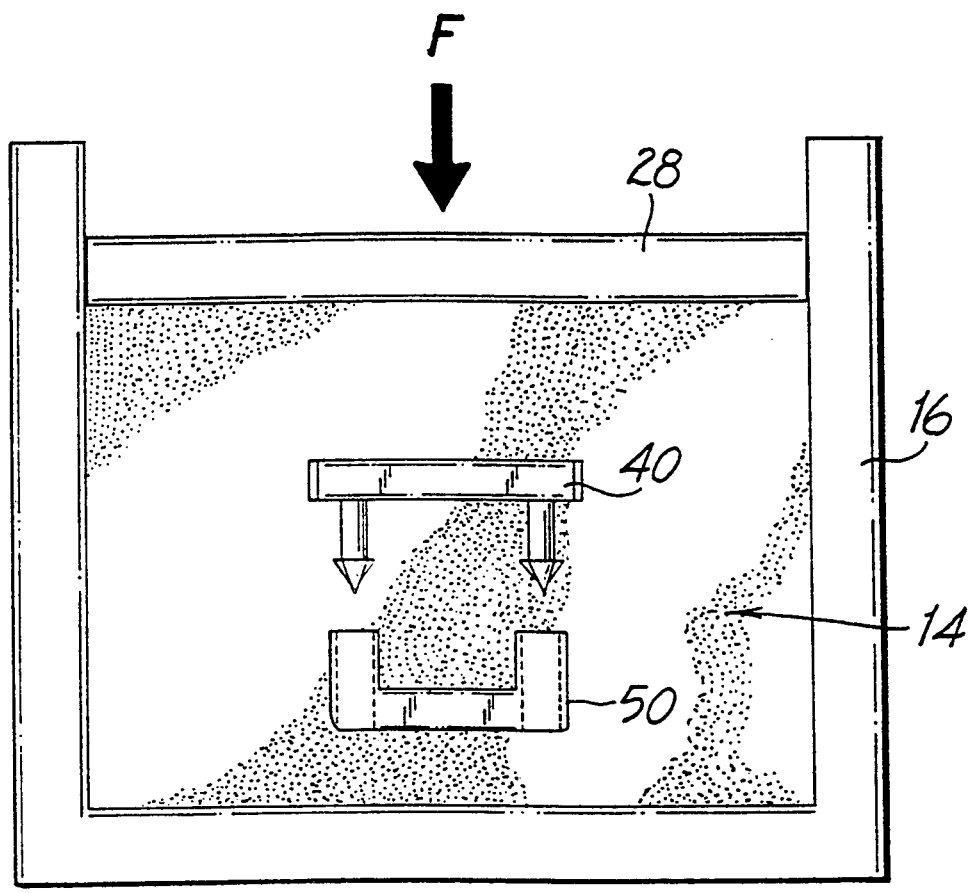
FIG. 3 is a diagrammatic elevational view of an apparatus employing the external pressurization method of the present invention.

FIG. 3 is a diagrammatic view of alternative ways to pressurize the support medium. The thermoplastic work pieces such as the aforementioned surgical fastener 40, and retainer 50, which are to be treated, are placed in particulate support medium 14 contained within a rigid container 16. As noted, support medium 14 is preferably fine powder, such as conditioned sodium bicarbonate or talc. Piston 28 presses downwardly upon the support medium 14 by means of an applied force F, which may be applied by hydraulic or pneumatic means, or by a spring means, or by dead weight.

The preferred sequence of operation is as follows. A quantity of powder support medium such as conditioned sodium bicarbonate or talc is placed in a cylindrical container and tamped down with piston 28 to produce a flat reference surface. Thermoplastic pieces such as surgical fasteners and retainers are placed on this surface and additional powder is applied and tamped. Alternate layers of support medium and plastic pieces are gradually built-up. Finally the piston is pressed down on the upper surface of the last layer of medium and secured by clamping means. The treatment process such as annealing is then performed as described hereinabove.

EXAMPLE 1

Sodium bicarbonate (baking soda) was conditioned in an oven in flat pans at 125° C. for 12 hours. After cooling, the powder was sifted through a #20 standard mesh screen and stored dry. An aluminum pan (7 in.×11 in.×1 in.) was partially filled with a layer of the conditioned sodium bicarbonate. Parts to be annealed were then pressed by hand into the conditioned sodium bicarbonate powder. Additional conditioned sodium bicarbonate was added to fill the pan and to fill the hollow and cut-out sections of the parts. A thin, finely porous material, namely a paper hairnet, was used to cover the pan to hold the powder in place while applying a vacuum.

The pan was placed in a Fairprene rubberized vacuum bag (11 in.×16 in. inside dimensions) equipped with a vacuum disconnect fitting. The open end of the bag was clamped tightly closed. The bag was then placed in a convection oven equipped with a vacuum line. The vacuum bag was connected to the vacuum line and evacuated (less than 1 Torr) and maintained under vacuum. The oven was heated to 100° C. for three hours, which was a sufficient temperature and time to crystallize the polymer.

When the heating cycle was completed, the vacuum bag and its contents were allowed to cool to room temperature before removing the pan. The contents of the pan were sifted on a standard 18 mesh screen to separate the parts from the powder. The parts were quickly rinsed in water to remove any traces of powder and then placed in a vacuum oven at less than 1 Torr to remove residual water.

EXAMPLE 2

In this example the shrinkage associated with the prior known fixturing method of annealing is compared with the shrinkage associated with the pressurized powder method of the present invention.

The pieces annealed by both methods were surgical fasteners constructed from 90% glycolide/10% lactide copolymer and are illustrated in FIGS. 4a and 4b. Each fastener 40 comprised a backspan 41 and two prongs 42 projecting from the backspan 41. The prongs 42 each had barbs 43 at their tips.

Three 12-piece lots of fasteners were provided, each lot of fasteners originating from a different lot of plastic construction material. The pieces were first measured in the unannealed state for six dimensions: backspan length, backspan width, backspan thickness, the distance between prongs, the distance between the end of the backspan and the prong, and the diameter of the prong.

Each lot was divided such that 6 pieces were fixture annealed in accordance with the prior known fixturing method and 6 pieces were powder annealed in accordance with the method of the present invention. After annealing each fastener was again measured with respect to the dimensions indicated above. The average percentage of shrinkage was determined in accordance with the following formula $$\% \text{ shrinkage} = \frac{(X_1 - X_2)}{X_1} \times 100$$

wherein
$X_1$ = the average of the measured dimensions prior to annealing
$X_2$ = the average of the measured dimensions after annealing
The results are tabulated in Table 1.

TABLE 1

| | Average Percentage of Shrinkage | |
|---|---|---|
| Lot | Fixtured Pieces | Pressurized Powder Supported Pieces |
| 1 | 6.7% | 2.4% |
| 2 | 5.8% | 3.2% |
| 3 | 2.8% | 1.5% |

The above results clearly indicate that the pressurized powder annealing method of the present invention is associated with significantly less shrinkage than the prior known fixturing method. Thus greater dimensional stability of finished end use products is clearly possible.

Figure 5:
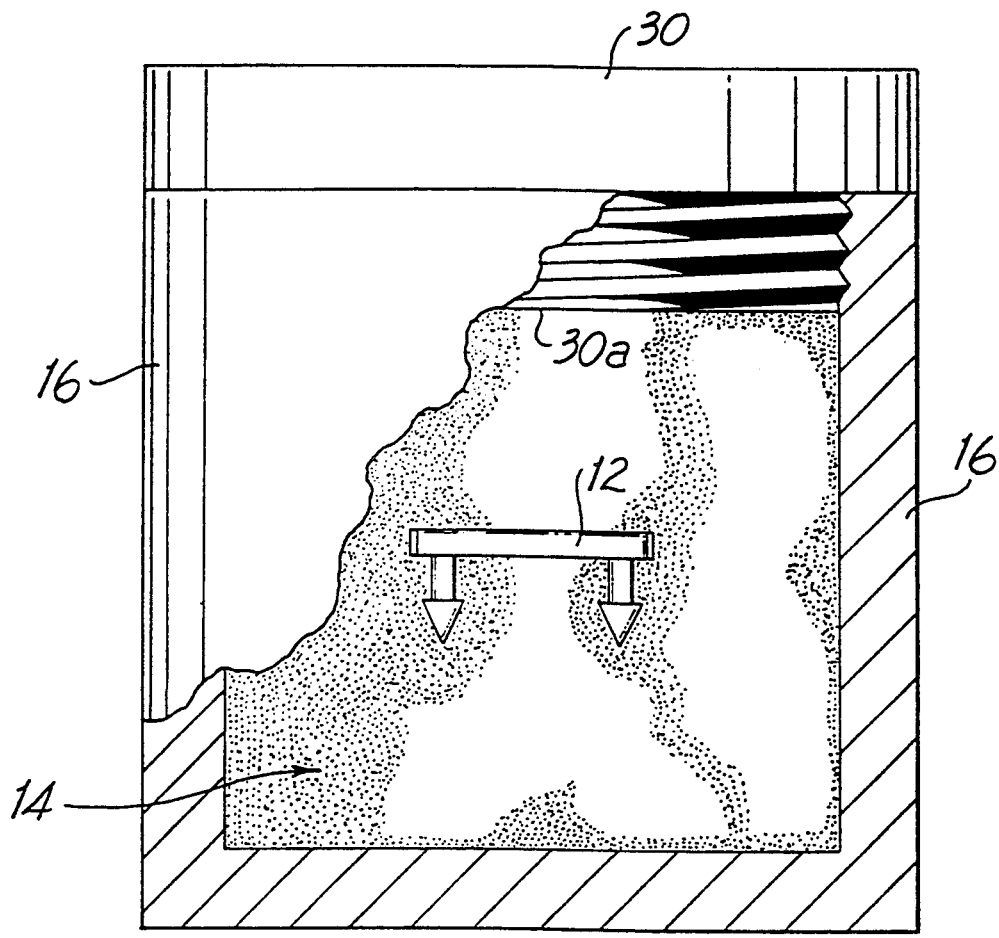
FIG. 5 is an elevational cut away view, partially in cross section of an apparatus employing the thermal method of the present invention.

In yet another embodiment of the present invention, as exemplified by FIG. 5, the pressure differential is not established by having a higher pressure external to the medium. Rather, a pressure differential is established between the powder medium and the object to be treated. Unlike the previously described embodiments in which the container was in some way deformable in response to a pressure differential between the interior and exterior (as, for example, by flexibility of the container or, if rigid, by means of a movable piston) so as to compress the support medium, the embodiment exemplified in FIG. 5 utilizes a difference in the coefficient of thermal expansion between the material which the particulate support comprises, and the material from which the container is made. A difference in thermal expansion will cause compression of the particulate support medium when the apparatus is subjected to a temperature change.

In FIG. 5, a powder medium 14 is tightly packed around a thermoplastic piece 12, and is contained in rigid container 16 which is sealed on all sides. Lid 30 and container 16, for example, may be coupled together by means of a threaded joint. The powder medium 14 occupies substantially all of the free space of the interior of the container. There is essentially no gap between the upper surface level of the powder medium 14 and the bottom surface 30a of the lid.

If the coefficient of thermal expansion of the support medium is greater than that of the container, the particulate medium will be compressed by placing the apparatus in a heating environment: the expanding particles are confined within a container which expands to a lesser degree.

Conversely, if the coefficient of thermal expansion of the container is greater than that of the particulate support medium, the particulate support medium will be compressed if the apparatus is cooled, the container contracting to a greater degree than that of the medium. The choice of materials, therefore, must be chosen to conform to the temperature requirements of the treatment process to be undergone. If the piece is to be subjected to an annealing process, and, therefore, heated to the appropriate temperature, the thermal expansion of the particulate medium must be greater than that of the container. Heating the apparatus will then cause the particulate medium to expand within a confined space, thereby creating a compression force on all sides of the piece while the piece is being treated.

The pressurized powder support of the present invention may be used for processes other than annealing plastic. For example, the particles can be employed as a carrier for a coating material. Various agents may be mixed with the powder medium for diffusion into the surface of the supported piece. The pressurized powder medium may be used to support pieces to be case hardened.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A method for annealing a surgical object comprising:
   a) providing a container;
   b) placing a particulate support medium with the container, said particulate support medium comprising an aggregation of substantially rigid particles of sufficiently small size to substantially conform to an outer surface of the object;
   c) placing an already formed surgical object in said particulate support medium in the container, said support medium thereby providing at least a bottom support for said surgical object, said surgical object being composed of a biocompatible thermoplastic material;
   d) placing additional particulate support medium within the container; and thereafter
   e) compacting the particulate support medium into a substantially rigid mass to substantially conform to the outer surface of said surgical object, said particulate support medium substantially enveloping said surgical object and supporting the surgical object within the container; and then
   f) applying heat for annealing the surgical object.

2. A method as recited in claim 1, wherein said step of compacting the support medium into a substantially rigid mass comprises the step of creating a difference between the pressure exterior to the aggregation of particles of the particulate support medium and the pressure inside the particulate support medium.

3. A method as recited in claim 1, wherein said container is substantially rigid on all sides and said particulate support medium and said container have relatively different coefficients of thermal expansion and the step of compacting said particulate support medium comprises changing the temperature of said particulate support medium and said container.

4. A method as recited in claim 1, wherein said surgical object is fully covered by said particulate support medium.

5. A method as recited in claim 1, wherein the step of placing the surgical object within the container further comprises the step of pressing the surgical object into the particulate support medium.

6. The method of claim 2, wherein the step of creating a difference between the pressure exterior to the aggregation of particles of the particulate support medium and the pressure inside the particulate support medium comprises applying a vacuum to the interior of the support medium.

7. The method of claim 1, wherein said particulate support medium comprises powdered talc.

8. The method of claim 1, wherein said particulate support medium comprises sodium bicarbonate.

9. The method of claim 1, wherein said particulate support medium remains porous after being compacted into a substantially rigid mass.

10. The method of claim 1, wherein said particulate support medium is water soluble.

11. A method for annealing a predetermined plurality of surgical objects comprising:
   (a) providing a container;
   (b) placing a layer of particulate support material within said container, said particulate support material comprising an aggregation of substantially rigid particles of sufficiently small size to substantially conform to an exterior surface of each of the surgical objects;
   (c) placing a plurality of already formed surgical objects within the container on said first layer of said support material, said first layer of support material providing at least a bottom support for said surgical objects, said surgical objects being composed of a bio-compatible thermoplastic material;
   (d) placing a second layer of particulate support material within the container to substantially cover said surgical objects; and thereafter,
   (e) compacting the support material into a substantially rigid mass to substantially conform to the outer surface of the objects and to support the surgical objects within the container; and then
   (f) applying heat for annealing the surgical objects.

12. A method as recited in claim 11, wherein said step of compacting the support medium into a substantially rigid mass comprises the step of creating a difference between the pressure exterior to the aggregation of particles of the particulate support material and the pressure inside the particulate support material.

13. A method as recited in claim 11, wherein said container is substantially rigid on all sides and said particulate support medium and said container have relatively different coefficients of thermal expansion and the stp of compacting said particulate support medium comprises changing the temperature of said particulate support medium and said container.

14. A method for annealing a surgical object comprising:
   (a) placing a particulate medium within a container, said medium adapted to support the surgical object and comprising an aggregation of substantially rigid particles of sufficiently small size to substantially conform to an outer surface of the surgical object,
   (b) placing an already formed surgical object within the container, the surgical object being composed of a biocompatible thermoplastic material; thereafter
   (c) compacting the particulate medium to rigidify the medium to conform the particulate medium to the outer surface of the surgical object to constrain the surgical object within the container; and then
   (d) applying heat for annealing the surgical object.

15. A method as recited in claim 14, wherein said step of compacting the support medium into a substantially rigid mass comprises the step of creating a difference between the pressure exterior to the aggregation of particles of the particulate support medium and the pressure inside the particulate support medium.

16. A method as recited in claim 14, wherein said container is substantially rigid on all sides and said particulate support medium and said container have relatively different coefficients of thermal expansion changing the temperature of said particulate support medium and said container.

17. A method as recited in claim 14, wherein said surgical object is fully covered by said particulate support medium.

18. A method as recited in claim 14, wherein the step of placing the surgical object within the container further comprises the step of pressing the surgical object into the particulate support medium.

19. A method of annealing a thermoplastic surgical article which is subject to deformation upon annealing, said method comprising:
   a) supporting the surgical article by placing the article in a particulate support medium which comprises an aggregation of substantially rigid particles of sufficiently small size to substantially conform to an outer surface of the surgical article, the support medium being within a container, and thereafter rigidifying the support medium by compacting means to conform the support medium to the outer surface of the surgical article; and then
   b) applying heat for annealing the surgical article;
   step (a) being performed so as to achieve a reduction of the deformation of the article as compared with an annealing method in which the article is supported by a non-particulate rigid holding means.

20. The method of claim 19, wherein said reduction of the deformation of the article is a reduction of at least about 35%.

21. The method of claim 19, wherein said reduction of the deformation of the article is a reduction of at least about 46%.

22. The method of claim 19, wherein the average deformation is no more than about 5.0%.

23. The method of claim 19, wherein the average deformation is no more than about 3.2%.

24. The method of claim 19, wherein said compacting means comprises creating a difference between the pressure exterior to said aggregation of particles in the support medium and the pressure within said aggregation of particles of the support medium.

25. The method of claim 24, wherein said container is flexible.

26. The method of claim 19, wherein said container is substantially rigid on all sides and said support medium and said container have relatively different coefficients of thermal expansion, and said compacting comprises changing the temperature of said support medium and said container.

* * * * *